US006592512B2

(12) United States Patent
Stöckert et al.

(10) Patent No.: US 6,592,512 B2
(45) Date of Patent: Jul. 15, 2003

(54) AT LEAST PARTIALLY IMPLANTABLE SYSTEM FOR REHABILITATION OF A HEARING DISORDER

(75) Inventors: Friedemann Stöckert, Münich (DE); Hans Leysieffer, Taufkirchen (DE)

(73) Assignee: Phonak AG, Stafa (CH)

(*) Notice: Subject to any disclaimer, the term of this patent is extended or adjusted under 35 U.S.C. 154(b) by 19 days.

(21) Appl. No.: 09/927,504

(22) Filed: Aug. 13, 2001

(65) Prior Publication Data

US 2002/0019668 A1 Feb. 14, 2002

(30) Foreign Application Priority Data

Aug. 11, 2000 (DE) ........................................ 100 39 401

(51) Int. Cl.[7] .......................... H04R 25/00; A61N 1/00; A61F 2/18

(52) U.S. Cl. .............................. 600/25; 623/10; 607/55

(58) Field of Search ..................... 600/25, 559; 607/55, 607/56, 57, 59, 60; 623/10, 11.11

(56) References Cited

U.S. PATENT DOCUMENTS 3,712,962 A 1/1973 Epley
3,870,832 A 3/1975 Fredrickson
3,882,285 A 5/1975 Nunley et al.
4,850,962 A 7/1989 Schaefer
5,015,225 A 5/1991 Hough et al.

(List continued on next page.)

FOREIGN PATENT DOCUMENTS

DE 198 27 898 11/1999
WO WO 98/06235 2/1998
WO WO 98/06236 2/1998
WO WO 98/06237 2/1998
WO WO 98/06238 2/1998

OTHER PUBLICATIONS

Zenner et al., "Active Electronic Hearing Implants for Patients with Conductive and Sensorineural Hearing Loss—New Era of Ea Surgery", pp. 749–774, 1997, HNO vol. 45.
Fredrickson et al., "Ongoing Investigations into an Implantable Electromagnetic Hearing Aid for Moderate to Severe Sensorineural Hearing Loss", pp. 107–120, 1995, Otolaryngologic Clinics of North America, vol. 28/1.
Leysieffer et al., "First Implantations of a Totally Implantable Electronic Hearing System for Sensorineural Hearing Loss", pp. 844–852 and pp. 853–863, 1998, HNO vol. 46.

(List continued on next page.)

*Primary Examiner*—David J. Isabella
(74) *Attorney, Agent, or Firm*—Nixon Peabody LLP; David S. Safran

(57) ABSTRACT

An at least partially implantable hearing system for rehabilitation of a hearing disorder, comprising at least one acoustic sensor for picking up an acoustic signal and converting it into an electrical audio sensor signal; an electronic signal processing unit for audio signal processing and amplification, the signal processing unit including an electronic driver arrangement; an electrical power supply unit which supplies individual components of the system with energy; and at least one electromechanical output transducer driven by the electronic driver arrangement and having a mechanical output impedance, said transducer being provided with an active electromechanical element and an output member for stimulating, via a passive coupling element, an ossicle of a middle ear ossicular chain, which chain has a natural capability for vibratory movement; wherein a switchable clutch arrangement is disposed between the active electromechanical element of the transducer and the passive coupling element, and wherein in an inactive condition of the electronic driver arrangement the clutch arrangement disconnects the passive coupling element from the output member of the transducer to such an extent that the mechanical output impedance of the transducer has substantially no influence on the natural capability of the ossicular chain for vibratory movement.

26 Claims, 4 Drawing Sheets

U.S. PATENT DOCUMENTS

| | | | |
|---|---|---|---|
| 5,277,694 | A | 1/1994 | Leysieffer et al. |
| 5,279,292 | A | 1/1994 | Baumann et al. |
| 5,554,096 | A | 9/1996 | Ball |
| 5,624,376 | A | 4/1997 | Ball et al. |
| 5,707,338 | A | 1/1998 | Adams et al. |
| 5,788,711 | A | 8/1998 | Lehner et al. |
| 5,814,095 | A | 9/1998 | Muller et al. |
| 5,941,814 | A | 8/1999 | Lehner et al. |
| 5,999,632 | A | 12/1999 | Leysieffer et al. |
| 6,077,215 | A | 6/2000 | Leysieffer |
| 6,113,531 | A | 9/2000 | Leysieffer et al. |
| 6,123,660 | A | 9/2000 | Leysieffer |
| 6,128,392 | A | 10/2000 | Leysieffer |
| 6,162,169 | A | 12/2000 | Leysieffer |
| 6,198,971 | B1 | 3/2001 | Leysieffer |

OTHER PUBLICATIONS

Leysieffer et al., "Ein Implantierbarer Piezoelektrischer Horgeratewandler fur Innenohrschwerhorige", pp. 792–800 1997, HNO vol. 45.

Yanighara et al., "Efficacy of the Partially Implantable Middle Ear Implant in Middle and Inner Ear Disorders", pp. 149–159, 1988, Advances in Audiology, vol. 4.

Suzuki et al., "Implantation of Partially Implantable Middle Ear Implant and the Indication", pp. 160–166, 1988, Advances in Audiology, vol. 4.

Maniglia et al., "Contactless Semi–Implantable Electromagnetic Middle Ear Device for the Treatment of Sensorineural Hearing Loss", pp. 121–141, 1995, Otolaryngologic Clinics of North America, vol. 28/1.

AT LEAST PARTIALLY IMPLANTABLE SYSTEM FOR REHABILITATION OF A HEARING DISORDER

BACKGROUND OF THE INVENTION

1. Field of the Invention

This invention relates to an at least partially implantable hearing system for rehabilitation of a hearing disorder comprising at least one acoustic sensor for picking up an acoustic signal and converting the acoustic signal into corresponding electrical audio sensor signals, an electronic signal processing unit for audio signal processing and amplification, an electrical power supply unit which supplies individual components of the system with energy, and at least one electromechanical output transducer driven by an electronic driver arrangement of the signal processing unit, wherein the electromechanical output transducer is provided with an active electromechanical element and an output member for stimulating, via a passive coupling element, an ossicle of a middle ear ossicular chain, which chain has a natural capability for vibratory movement.

2. Description of Related Art

Hearing systems are defined here as systems in which the acoustic signal is picked up with at least one sensor which converts the acoustic signal into an electrical signal (microphone function), which is electronically further processed and amplified, and whose output-side signal stimulates the damaged hearing electromechanically.

The expression "hearing disorder" is defined here as inner ear damage, combined inner ear and middle ear damage, and a temporary or permanent noise impression (tinnitus).

Electronic measures for rehabilitation of inner ear damage which cannot be cured by surgery have currently achieved great importance. With total failure of the inner ear, cochlear implants with direct electrical stimulation of the remaining auditory nerves are in routine clinical use. For medium to severe inner ear damage, for the first time, fully digital hearing devices are presently being used which open up a new world of electronic audio signal processing and offer expanded possibilities of controlled audiological fine tuning of the hearing devices to the individual inner ear damage. In spite of major improvements of hearing aid hardware achieved in recent years, in conventional hearing aids, there remain basic defects which are caused by the principle of acoustic amplification, i.e. especially by the reconversion of the electronically amplified signals in airborne sound. These defects include aspects such as the visibility of the hearing aids, poor sound quality as a result of electromagnetic transducers (speakers), closed external auditory canal as well as feedback effects with high acoustic gain.

As a result of these fundamental defects, there has long been the desire to move away from conventional hearing aids with acoustic stimulation of the damaged inner ear and to replace them by partially or fully implantable hearing systems with direct mechanical stimulation. Implantable hearing systems differ from conventional hearing aids: the acoustic signal is converted with a proper microphone into an electrical signal and amplified in an electronic signal processing stage; this amplified electrical signal, however, is not sent to an electroacoustic transducer (speaker), but to an implanted electromechanical transducer providing for output-side mechanical vibrations which are sent directly, therefore with direct mechanical contact, to the middle ear or inner ear, or indirectly via an air gap in, for example, electromagnetic converter systems. This principle applies regardless of whether implantation of all necessary system elements is partial or complete and also regardless of whether an individual with pure inner ear impairment with a completely intact middle ear or an individual with combined hearing impairment, in which the middle and inner ear is damaged, is to be rehabilitated. Therefore implantable electromechanical transducers and methods for coupling the mechanical transducer vibrations to the functioning middle ear or directly to the inner ear for rehabilitation of a pure inner ear impairment, or to a remaining ossicle of the middle ear in the case of an artificially or pathologically altered middle ear for taking care of a hearing disorder caused by a disturbance of sound conduction, or for combinations of such disorders, have been described in the recent scientific literature and in many patents.

Useful electromechanical transducer processes include basically all physical transducer principles, such as electromagnetic, electrodynamic, magnetostrictive, dielectric and piezoelectric. Various research groups, in recent years, have focused essentially on two of these processes, namely electromagnetic and piezoelectric processes. A survey can be found in ZENNER and LEYSIEFFER (HNO 10/1997, vol. 45, pp. 749–774).

In the piezoelectric process, direct mechanical coupling of the output-side transducer vibrations to the middle ear ossicle or to the oval window is essential. In the electromagnetic principle, force coupling between the transducer and ossicle, on the one hand, can take place "without contact", i.e. via an air gap; in this case, only the permanent magnet is caused to vibrate by the transducer being in direct mechanical contact with the middle ear ossicle by permanent fixation. On the other hand, it is possible to implement the transducer entirely in a housing (in this case the coil and the magnet preferably being coupled with the smallest possible air gap) and to transmit the output-side vibrations via a mechanically stiff coupling element with direct contact to the middle ear ossicle (see FREDRICKSON et al.: *Ongoing investigations into an implantable electromagnetic hearing aid for moderate to severe sensorineural hearing loss*; Otolaryngologic Clinics of North America, Vol. 28/1 (1995), pp. 107–121; and Leysieffer et al., HNO 10/97, vol. 45, pp.792–800).

The patent literature contains some of the aforementioned versions of both electromagnetic and also piezoelectric hearing aid transducers: U.S. Pat. No. 3,712,962, EPLEY; U.S. Pat. No. 3,870,832, FREDRICKSON; U.S. Pat. No. 3,882,285, NUNLEY et al.; U.S. Pat. No. 4,850,962, SCHAEFER; U.S. Pat. No. 5,015,224, MANIGLIA; U.S. Pat. No. 5,277,694, LEYSIEFFER et al.; U.S. Pat. No. 5,554,096, BALL; U.S. Pat. No. 5,707,338, ADAMS et al.; U.S. Pat. No. 6,123,660, LEYSIEFFER; U.S. Pat. No. 6,162,169, LEYSIEFFER; International Patent Application Publications WO-A 98/06235, ADAMS et al.; WO-A 98/06238, ADAMS et al.; WO-A 98/06236, KROLL et al.; WO-A 98/06237, BUSHEK et al.

The partially implantable piezoelectric hearing system of the Japanese group of Suzuki and Yanigahara presupposes, for implantation of the transducer, the absence of the middle ear ossicles and a free tympanic cavity to be able to couple the piezo element to the stapes (Yanigahara et al.: *Efficacy of the partially implantable middle ear implant in middle and inner ear disorders*: Adv. Audiol., Vol. 4, Karger Basel (1988), pp. 149–159; Suzuki et al.: *Implantation of partially implantable middle ear implant and the indication*. Adv. Audiol., Vol. 4, Karger Basel (1988), pp. 160–166). Likewise, in the method of implanting a hearing system for inner ear hearing-impaired according to SCHAEFER (U.S.

Pat. No. 4,850,962) basically the incus is removed in order to be able to couple a piezoelectric transducer element to the stapes. This also applies to further developments which are based on the SCHAEFER technology and which are described in the above mentioned patents (U.S. Pat. No. 5,707,338, ADAMS et al.; International Patent Application Publications WO-A 98/06235, ADAMS et al.; WO-A 98/06238, ADAMS et al.; WO-A 98/06236, KROLL et al.; WO-A 98/06237, BUSHEK et al.).

The BALL electromagnetic transducer ("Floating Mass Transducer FMT" of U.S. Pat. No. 5,554,096, BALL; U.S. Pat. No. 5,624,376, BALL et al.) is, on the other hand, directly fixed to the long process of the incus when the middle ear is intact. The electromagnetic transducer of the partially implantable system of FREDRICKSON (Fredrickson et al.: *Ongoing investigations into an implantable electromagnetic hearing aid for moderate to severe sensorineural hearing loss*, Otolaryngologic Clinics of North America, Vol. 28/1 (1995), pp. 107–121) is directly mechanically coupled to the body of the body of the incus when the ossicular chain of the middle ear is likewise intact. The same applies to the piezoelectric transducers of LEYSIEFFER (LEYSIEFFER et al.: *An implantable piezoelectric hearing aid converter for the inner ear hearing-impaired*. HNO 1997/45, pp. 792–800; U.S. Pat. No. 5,277,694, LEYSIEFFER et al.; U.S. Pat. No. 6,123,660, LEYSIEFFER; U.S. Pat. No. 6,162,169, LEYSIEFFER). Also in the electromagnetic transducer system of MANIGLIA (MANIGLIA et al.: *Contactless semi-implantable electromagnetic middle ear device for the treatment of sensorineural hearing loss*, Otolaryngologic Clinics of North America, Vol. 28/1 (1995), pp. 121–141) with the ossicular chain intact a permanent magnet is permanently mechanically fixed to the ossicular chain, but is mechanically driven via an air gap coupling by a coil.

In the described transducer and coupling versions, basically, two implantation principles can be distinguished:

a) In the case of the one principle the electromechanical transducer with its active transducer element is located itself in the middle ear region in the tympanic cavity and the transducer is directly connected there to an ossicle or the inner ear (U.S. Pat. Nos. 4,850,962, 5,015,225, 5,707,338, 5,624,376, 5,554,096, and International Patent Application publication Nos. WO 98/06235, WO 98/06238, WO 98/06236, and WO 98/06237).

b) In the other principle the electromagnetic transducer with its active transducer element is located outside of the middle ear region in an artificially formed mastoid cavity; the output-side mechanical vibrations are then transmitted to the middle or inner ear by means of mechanically passive coupling elements via suitable surgical accesses (the natural aditus ad antrum, opening of the chorda-facialis angle or via an artificial hole from the mastoid) (Fredrickson et al.: *Ongoing investigations into an implantable electromagnetic hearing aid for moderate to severe sensorineural hearing loss*. Otolaryngologic Clinics of North America, Vol. 28/1 (1995), pp. 107–121; U.S. Pat. No. 5,277,694; U.S. Pat. No. 6,123,660; U.S. Pat. No. 6,162,169).

An advantage of the a) type versions is, that the transducer can be made as a so-called "floating mass" transducer, i.e., the transducer element does not require any "reaction" via secure screwing to the skull bone, but it vibrates based on the laws of mass inertia with its transducer housing and transmits these vibrations directly to a middle ear ossicle (U.S. Pat. Nos. 5,624,376, 5,554,096, and 5,707,338, and International Patent Application publication no. WO 98/06236). On the one hand, this means that an implantable fixation system on the cranial vault can be advantageously omitted; on the other hand, this version disadvantageously means that bulky artificial elements must be placed in the tympanic cavity, and their long-term stability and biostability are currently not known or guaranteed, especially in the case of temporary pathological changes of the middle ear (for example, otitis media). Another major disadvantage is that the transducer together with its electrical supply line has to be transferred from the mastoid into the middle ear and must be fixed there using suitable surgical tools; this requires an expanded access through the chorda facialis angle, and thus, entails a latent hazard to the facial nerve which is located in the immediate vicinity. Furthermore, such "floating mass" transducers can be used merely in a very limited manner or not at all, when the inner ear is to be directly stimulated for example via the oval window, or when, due to pathological changes, for example the incus is substantially damaged or is no longer present, so that such a transducer no longer can be mechanically connected to an ossicle that is able to vibrate and is in connection with the inner ear.

A certain disadvantage of the transducer versions as per b) is that the transducer housing is to be attached to the cranial vault with the aid of implantable positioning and fixation systems (advantageous embodiment U.S. Pat. No. 5,788,711). A further disadvantage of the transducer versions as per b) is that a recess is to be made, preferably by an appropriate laser, in the respective ossicle in order to allow the application of the coupling element. This, on the one hand, is technically complicated and expensive and, on the other hand, involves risks for the patient. Both in the partially implantable system of FREDRICKSON (*"Ongoing investigations into an implantable electromagnetic hearing aid for moderate to severe sensorineural hearing loss"*, Otolaryngologic Clinics of North America, Vol. 28/1 (1995), pp. 107–121) as well as in the fully implantable hearing system of LEYSIEFFER and ZENNER (HNO 1998, vol. 46, 853–863 and 844–852), when the vibrating transducer part is coupled to the body of the incus, it is assumed that for permanent and mechanically secure vibration transmission the tip of the coupling rod which is placed in the laser-induced depression of the middle ear ossicle undergoes osseointegration over the long term, i.e., the coupling rod coalesces solidly with the ossicle and thus ensures reliable transmission of dynamic compressive and tensile forces. However, this long-term effect is currently not yet scientifically proven or certain. Furthermore, in this type of coupling, in case of a technical transducer defect, there is the disadvantage that decoupling from the ossicle to remove the transducer can only be done with mechanically based surgical methods; this can mean considerable hazard to the middle ear and especially the inner ear. Therefore further coupling elements, partly involving novel surgical access paths, were developed which minimize or no longer have the above mentioned disadvantages (U.S. Pat. No. 5,941,814, LEHNER et al., commonly owned U.S. patent application Ser. Nos. 09/576,009; 09/613,560; 09/626,745; 09/680,489).

The major advantage of these converter embodiments as per b), however, is that the middle ear remains largely free and coupling access to the middle ear can take place without major possible hazard to the facial nerve. One preferable surgical process for this purpose is described in U.S. Pat. No. 6,077,215, LEYSIEFFER. Basic advantageous forms of passive coupling elements for transmission of the output-side transducer vibrations from the mastoid to the middle ear or inner ear are described in U.S. Pat. Nos. 5,277,694 and 5,941,814.

In the last years partially and fully implantable hearing systems of the above described type were chronically implanted in human patients. The long-time results show the following effects:

for the implantation of the "floating mass" transducer (FMT) and the use of a partial implant it could be demonstrated in a statistically significant manner that the residual audition is not or only slightly impaired by the implantation of the FMT as long as the driver electronics of the implant are switched off, because this transducer has a very low mass which is in the order of the mass of the ossicle itself, and that in view of the "floating" principle of the transducer a stiffening of the ossicular chain does not occur or occurs to a minor extent only (e.g. because of the stiffness of the transducer feed line);

in the implantation of mechanically directly coupled transducers in conformity with the above discussed embodiments as per b) it turned out that particularly in the case of transducers based on the piezoelectric principle and with high mechanical output impedance (U.S. Pat. No. 5,277,694) the residual audition may be distinctly reduced when the driver electronics are switched off, because in this case the high mechanical output impedance of the transducer dominates at the site of coupling to the ossicular chain and therefore the acoustic energy irradiated via the tympanic membrane is substantially reflected at the site of coupling.

Today, the aspect of essentially maintaining the acoustic residual audition is considered to be of importance, particularly when, in view of the design of the entire implant system, an interruption of the ossicular chain to avoid feedback or/and to optimize the transmission of energy into the inner ear is not provided for. Such an implant design e.g. may consist in providing a digital signal processor and software-based algorithms to avoid or substantially reduce feedback effects (U.S. Pat. No. 6,128,392).

Basically it is therefore desired to use an arrangement which, by preventing the ossicle from being "braked to standstill" by the transducer coupled thereto, as far as possible retains the residual audition when the electronic implant system is inoperative, particularly when using mechanically directly coupled electromagnetic transducers for implantable hearing systems having a mechanical output impedance which is higher than the mechanical load impedance of the middle and/or inner ear structure coupled thereto. Maintaining the residual audition here is to be understood to the effect that the sound energy incoming via the external ear is picked up via the tympanic membrane largely undiminished, and is transmitted to the inner ear as mechanical vibratory energy.

Possible proposals of solution therefor are disclosed in commonly owned U.S. patent application Ser. Nos. 09/576,009 and 09/626,745, where the vibrating output element of an electromechanical transducer having a high mechanical output impedance is not directly coupled to the selected ossicle by metallic contact; rather coupling is effected through adhesion forces or via an entropy-elastic intermediate layer made e.g. of silicone. Thereby the mechanical source impedance of the transducer is reduced. A further advantage of such a coupling, e.g. an adhesion coupling, is that the ossicle is not "restrained" mainly in the direction of vibration of the driving transducer, since such "restraint" can lead to a less than optimum form of vibration of the footplate of the stapes in the oval window. (One preferable form of vibration is a piston-like vibration of the footplate of the stapes perpendicular to its plane). Rather, the ossicle sets itself its (frequency-dependent) direction of vibration based on the dynamic properties of the intact middle ear. This advantage also applies to a non-intact, (partially) decomposed ossicular chain and coupling to the "remainder" of the chain facing the inner ear, and in the extreme case, also to only a residual stapes or only the footplate of the stapes since it is suspended by the so-called ligament (the elastic annular ligament which "holds" the stapes in the oval window). So far, however, there are no practical experiences with such an approach and thus no proof for the functionality thereof as to the main aspect of the subject invention.

SUMMARY OF THE INVENTION

A primary object of the present invention is to devise an at least partially implantable hearing system which maintains in a particularly reliable manner the residual audition of the user of the hearing system when the electronic implant system is inoperative.

This object is achieved in that, in an at least partially implantable hearing system for rehabilitation of a hearing disorder comprising at least one acoustic sensor for picking up an acoustic signal and converting the acoustic signal into corresponding electrical audio sensor signals, an electronic signal processing unit for audio signal processing and amplification, an electrical power supply unit which supplies individual components of the system with energy, and at least one electromechanical output transducer driven by an electronic driver arrangement of the signal processing unit, wherein the electromechanical output transducer is provided with an active electromechanical element and an output member for stimulating, via a passive coupling element, an ossicle of a middle ear ossicular chain, which chain has a natural capability for vibratory movement, according to the invention, a switchable clutch arrangement is disposed between the active electromechanical element of the transducer and the passive coupling element, wherein in an inactive condition of the electronic driver arrangement the clutch arrangement disconnects the passive coupling element from the output member of the transducer to such an extent that the mechanical output impedance of the transducer has substantially no influence on the natural capability of the ossicular chain for vibratory movement.

When in the hearing system of the invention the electronic implant system is inactive, i.e. inoperative, for whatever reason, the active electromechanical element of the transducer is decoupled from the passive coupling element and thus from the ossicular chain. This avoids that vibrations of the ossicular chain resulting from acoustic signals are impaired or prevented by the electromechanical transducer which otherwise, i.e. during normal operation of the hearing system, is mechanically directly coupled to the ossicular chain, or, stated otherwise, that acoustic energy which is incoming via the tympanic membrane is reflected to a substantial extent at the coupling site. Accordingly, the sound energy which enters through the external ear and which is picked up by the tympanic membrane is transmitted to the inner ear substantially without reduction. Therefore, the residual audition of the user of the hearing system is maintained to a substantial extent.

The solution in accordance with the invention is of particular importance when the hearing system has a mechanical output impedance which is higher than the mechanical load impedance of the biological middle ear and/or inner ear structure coupled thereto.

The term "switchable" used here in connection with the clutch arrangement is to be understood in a broad sense. It is by no means restricted to a force- or form-locking interconnection in the "switched on" condition, and a complete separation of the active electromechanical transducer element from the passive coupling element in the "switched off" condition of the clutch arrangement. Rather it is intended to generally include all cases in which there is a substantial difference between the "switched on" condition and the "switched off" condition of the switchable clutch arrangement as to the mechanical output impedance of the output transducer—in relation to the side of the clutch arrangement remote from the transducer. Preferably, the switchable clutch arrangement is designed such that there is a difference of at least 10 dB in the mechanical load impedance between switched-on condition and the switched-off condition of the clutch arrangement.

In view of the confined space situation at the site of implantation and in order to keep the vibrating masses small, the switchable clutch arrangement is preferably manufactured using Microsystems engineering techniques, for example, photolithography. Advantageously, the clutch arrangement comprises an electromechanically active member, particularly a piezoelectric element. The active electromechanical element of the transducer and the clutch arrangement may be housed in a common casing. This simplifies controlling of the clutch arrangement and avoids an additional clutch casing.

The passive coupling element and the active electromechanical element of the transducer may be mechanically interconnected in a known manner via a coupling rod. In that case the clutch arrangement may be incorporated into the coupling rod or disposed between the active electromechanical element of the transducer and the end of the coupling rod facing the transducer.

Preferably, the electronic signal processing unit is designed to also control the clutch arrangement. Advantageously, the signal processing unit comprises a digital signal processor which provides for controlling the clutch arrangement as well as for processing the audio sensor signals and/or for generation of digital signals for tinnitus masking.

The signal processing unit can be designed to be static such that as a result of scientific findings respective software modules are filed once in a program storage of the signal processor and remain unchanged. But then if later, for example due to more recent scientific findings, improved algorithms for signal processing are available and these improved algorithms are to be used, the entire implant or implant module which contains the corresponding signal processing unit must be replaced by a new unit with the altered operating software by invasive surgery on the patient. This surgery entails renewed medical risks for the patient and is very complex.

This problem can be solved in that, in another embodiment of the invention, a rewritable implantable storage arrangement is assigned to the signal processor for storage and retrieval of an operating program and at least parts of the operating program are adapted to be at least partially replaced or changed by data transmitted from an external unit via a telemetry means. In this way, after implantation of the implantable system the operating software as such can be changed or completely replaced, as is explained for otherwise known systems for rehabilitation of hearing disorders in U.S. Pat. No. 6,198,971.

Preferably, the design is such that, in addition, for fully implantable systems, in the known manner, operating parameters, i.e., patient-specific data, for example, audiological adaption data, or variable implant system parameters (for example, as a variable in a software program for controlling the clutch arrangement or for control of battery recharging) can be transmitted transcutaneously into the implant after implantation, i.e., wirelessly through the closed skin, and thus, can be changed. Here, preferably, the software modules are designed to be dynamic or re-programmable to provide for an optimum rehabilitation of the respective hearing disorder. In particular, the software modules can be designed to be adaptive, and parameter matching can be done by training by the implant wearer and optionally by using other aids.

Furthermore, the signal processing electronics can contain a software module which achieves simulation as optimum as possible based on an adaptive neural network. Training of this neural network can take place again by the implant wearer and/or using other external aids.

The storage arrangement for storage of operating parameters and the storage arrangement for storage and retrieval of the operating program can be implemented as storages independent of one another; however there can also be a single storage in which both the operating parameters and also operating programs can be filed.

The subject approach allows matching of the system to circumstances which can be detected only after implantation of the implantable system. Thus, for example, in an at least partially implantable hearing system for rehabilitation of a monaural or binaural inner ear disorder and of a tinnitus by mechanical stimulation of the inner ear, the sensoric (acoustic sensor or microphone) and actoric (output stimulator) biological interfaces are always dependent on anatomic, biological and neurophysiological circumstances, for example on the interindividual healing process. These interface parameters can also be individual, also especially time-variant. Thus, for example the transmission behavior of an implanted microphone can vary interindividually and individually as a result of being covered by tissue, and the transmission behavior of an electromechanical transducer which is coupled to the inner ear can vary in view of on different coupling qualities. These differences of interface parameters which cannot be eliminated or reduced in the devices known from the prior art even by replacing the implant can now be optimized by changing or improving the signal processing of the implant.

In an at least partially implantable hearing system, it can be advisable or become necessary to implement signal processing algorithms which have been improved after implantation. Especially the following should be mentioned here:

- speech analysis processes (for example, optimization of a fast Fourier transform (FFT))
- static or adaptive noise detection processes
- static or adaptive noise suppression processes
- processes for optimization of the signal to noise ratio within the system
- optimized signal processing strategies in progressive hearing disorder
- output level-limiting processes for protection of the patient in case of implant malfunctions or external faulty programming
- processes of preprocessing of several sensor (microphone) signals, especially for binaural positioning of the sensors
- processes for binaural processing of two or more sensor signals in binaural sensor positioning, for example optimization of spacial hearing or spacial orientation phase or group delay time optimization in binaural signal processing processes for optimized driving of the output stimulators, especially for binaural positioning of the stimulators.

Among others, the following signal processing algorithms can be implemented with this system even after implantation:

processes for feedback suppression or reduction processes for optimization of the operating behavior of the output transducer(s) (for example, optimization of the frequency response and phase response, improvement of the impulse response)

speech signal compression processes for sensorineural hearing loss signal processing methods for recruitment compensation in sensorineural hearing loss.

Furthermore, in implant systems with a secondary power supply unit, i.e., a rechargeable battery system, but also in systems with primary battery supply it can be assumed that these electrical power storages will enable longer and longer service lives and thus increasing residence times in the patients as technology advances. It can be assumed that fundamental and applied research for signal processing algorithms will make rapid progress. The necessity or the patent desire for operating software adaptation and modification will therefore presumably take place before the service life of the implanted power source expires. The system described here allows this adaptation of the operating programs of the implant even when the implant has already been implanted.

Preferably, there can furthermore be provided a buffer storage arrangement in which data transmitted from the external unit via the telemetry means can be buffered before being relayed to the signal processor. In this way the transmission process from the external unit to the implanted system can be terminated before the data transmitted via the telemetry means are relayed to the signal processor.

Furthermore, there can be provided checking logic which checks the data stored in the buffer storage arrangement before relaying the data to the signal processor. There can be provided a microprocessor module, especially a microcontroller, for control of the A/D-converters and/or the D/A converters and/or the signal processor within the implant via a data bus, preferably the checking logic and the buffer storage arrangement being implemented in the microprocessor module, and wherein also program parts or entire software modules can be transferred via the data bus and the telemetry means between the outside world, the microprocessor module and the signal processor.

An implantable storage arrangement for storing the working program for the microprocessor module is preferably assigned to the microprocessor module, and at least parts of the working program for the microprocessor module can be changed or replaced by data transmitted from the external unit via the telemetry means.

In another embodiment of the invention, at least two storage areas for storage and retrieval of at least the operating program of the signal processor may be provided. This contributes to the reliability of the system, in that due to the multiple presence of a storage area which contains the operating program(s), for example, after transmission from the exterior or when the implant is turned on, checking for the absence of faults in the software can be done.

Analogously to the above, the buffer storage arrangement can also comprise at least two storage areas for storage and retrieval of data transferred from the external unit via the telemetry means, so that after data transmission from the external unit still in the area of the buffer storage the absence of errors in the transferred data can be checked. The storage areas can be designed for example for complementary filing of the data transferred from the external unit. At least one of the storage areas of the buffer storage arrangement however can also be designed to store only part of the data transferred from the external unit, wherein in this case the absence of errors in the transferred data is checked in sections.

Furthermore, to ensure that in case of transmission errors, a new transmission process can be started, a preprogrammed read-only memory area which cannot be overwritten can be assigned to the signal processor, in which ROM area the instructions and parameters necessary for "minimum operation" of the system are stored, for example, instructions which after a "system crash" ensure at least error-free operation of the telemetry means for receiving an operating program and instructions for its storage in the control logic.

As already mentioned, the telemetry means is advantageously designed not only for reception of operating programs from the external unit but also for transfer of operating parameters between the implantable part of the system and the external unit such that on the one hand such parameters (for example the volume) can be adjusted by a physician, a hearing aid acoustics specialist or the wearer of the system himself, and on the other hand the system can also transfer the parameters to the external unit, for example to check the status of the system.

A totally implantable hearing system of the aforementioned type can have on the implant side in addition to the actoric stimulation arrangement and the signal processing unit at least one implantable acoustic sensor and a rechargeable electrical storage element, and in this case a wireless transcutaneous charging device can be provided for charging of the storage element. For a power supply there can also be provided a primary cell or another power supply unit which does not require transcutaneous recharging. This applies especially when it is considered that in the near future mainly by continuing development of processor technology a major reduction in power consumption for electronic signal processing can be expected so that for implantable hearing systems new forms of power supply will become usable in practice, for example power supply which uses the Seebeck effect, as is described in U.S. Pat. No. 6,131,581. Preferably, there is also provided a wireless remote control for control of the implant functions by the implant wearer.

In case of a partially implantable hearing system, at least one acoustic sensor, an electronic signal processing arrangement, a power supply unit and a modulator/transmitter unit are contained in an external module which can be worn outside on the body, especially on the head over the implant. The implant comprises the output-side electromechanical transducer and the intracochlear stimulation electrode array, but is passive in terms of energy and receives its operating energy and transducer control data via the modulator/transmitter unit in the external module.

The described system can be designed to be monaural or binaural for the fully implantable design as well as for the partially implantable design. A binaural system for rehabilitation of a hearing disorder of both ears has two system units which each are assigned to one of the two ears. In doing so the two system units can be essentially identical to one another. However, one of the system units can also be designed as a master unit and the other system unit as a slave unit which is controlled by the master unit. The signal processing modules of the two system units can communicate with one another in any way, especially via a wired implantable line connection or via a wireless connection, preferably a bidirectional high frequency path, a ultrasonic path coupled by bone conduction, or a data transmission path which uses the electrical conductivity of the tissue of the implant wearer such that in both system units optimized binaural signal processing and transducer array control are achieved.

These and further objects, features and advantages of the present invention will become apparent from the following description when taken in connection with the accompanying drawings which, for purposes of illustration only, shows several embodiments in accordance with the present invention.

DETAILED DESCRIPTION OF THE INVENTION

Figure 1:
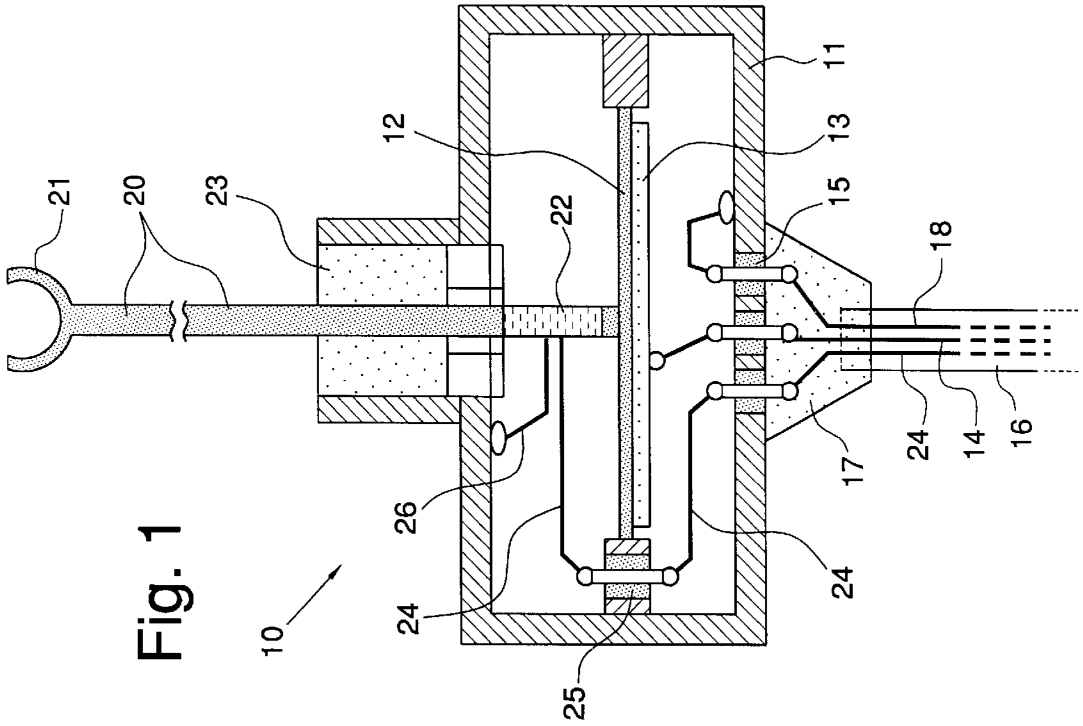
FIG. 1 shows an embodiment of a piezoelectric output transducer system for stimulation of a preselected middle ear ossicle, the system including an electrically actuated clutch arrangement.

The implantable electromechanical output transducer 10 illustrated in FIG. 1 is provided with a biocompatible cylindrical housing 11 of electrically conductive material, such as titanium. The housing 11 is filled with an inert gas. An electrically conductive membrane 12 that can oscillate, is disposed within the housing 11. The membrane 12 preferably is circular, and it is fixedly connected to housing 11 at the outer edge thereof. A thin disk 13 of piezoelectric material, e.g. lead-zirconate-titanate (PTZ), is provided at the side of membrane 12, which in FIG. 1 is the underside. The side of the piezoelectric disk 13 facing membrane 12 is in electrically conductive connection with membrane 12, preferably via an electrically conductive adhesive connection. The piezoelectric disk 13 is contacted, at the side thereof remote from membrane 12, with a thin flexible wire which is part of a signal line 14 and which in turn is connected via a hermetically sealed housing lead-through 15 to a transducer line 16 which is disposed outside of housing 11. A polymer sealing between the outer side of housing 11, the housing lead-through 15 and the transducer line 16 is shown in FIG. 1 at 17. A ground terminal 18 extends from transducer line 16 via the housing lead-through 15 to the inner side of housing 11.

Application of an electrical voltage between the signal line 14 and the ground terminal 18 results in a deformation of the hetero-compound consisting of membrane 12 and piezoelectric disk 13, and thus in a deflection of membrane 12. Further particulars of such a piezoelectric transducer which may be utilized in the present system, too, are described in commonly owned U.S. Pat. No. 5,277,694 which is hereby incorporated by reference. Such an electromechanical output transducer typically has a relatively high mechanical output impedance, particularly a mechanical output impedance which is higher than the mechanical load impedance of the biological structure of the middle ear and/or the inner ear coupled to the transducer in the implanted state.

In the illustrated embodiment a coupling rod 20 and a passive coupling element 21 are provided to connect the transducer 10 to any desired middle ear ossicle. The passive coupling element 21 is attached to the end of coupling rod 20 remote from transducer 10 or is defined by this end of the coupling rod. The direct coupling of the output side of transducer 10 to the preselected ossicle takes place via a switchable clutch arrangement 22 which is in mechanical connection with the side of membrane 12 which in FIG. 1 is the upper side of membrane 12; preferably the connection is with the center of the membrane. The clutch arrangement 22, with its end facing the membrane 12, may directly engage membrane 12; however, clutch arrangement 22 also may be integrated into coupling rod 20.

In the illustrated embodiment coupling rod 20 extends at least approximately normal to membrane 12 from the outside into the interior of housing 11 through an elastically resilient polymer sealing 23. The polymer sealing 23 is designed such as to permit in the implanted state axial oscillations of the coupling rod 20. The clutch arrangement 22 is disposed within housing 11. A control line extends from the transducer line 16 through the housing lead-through 15 and a lead-through 25 within the housing 11 to the clutch arrangement 22. Clutch arrangement 22 furthermore is in electrically conductive connection with housing 11 via a ground terminal 26 and via housing 11 with ground terminal 18.

During normal operation of a hearing system incorporating the arrangement according to FIG. 1, the clutch arrangement 22 is switched on (i.e. engaged) under the influence of a signal applied via control line 24. The terms "switched on" or "engaged" here are to be understood to the effect that the clutch arrangement 22 provides for an at least approximately force- and/or shape-locking interconnection between membrane 12 and coupling rod 20 with respect to the vibratory movements which are caused by signals on the signal line 14 and which are required for an adequate hearing impression.

When, however, the hearing system is inactive for whatever reason, for example because the energy supply of the hearing system is depleted, the hearing system is defective or the hearing system is voluntarily switched off, the ossicles are "braked" by the transducer 10 due to the mechanical output impedance of the transducer 10 which impedance is relatively high in comparison to the mechanical load impedance of the biological middle or inner ear structure coupled to the transducer. This means that in such a case the hearing system impairs or totally suppresses a possibly still existent residual audition of the implant wearer.

The latter presently may be effectively counteracted by means of the clutch arrangement 22. Particularly, clutch arrangement 22 is switched off or is disengaged when the hearing system is inactive, thereby decoupling the transducer 10 from the biological middle or inner ear structure. The terms "switched off" or "disengaged" clutch arrangement and "decoupled" output transducer, respectively, here are to be understood to describe a state in which the mechanical output impedance of the transducer has no or only little effect on the natural ability of the ossicular chain of the middle ear to oscillate. Therefore the natural residual audition for airborne sound is substantially maintained when the clutch arrangement 22 is switched off. Preferably, the clutch arrangement 22 is designed such that there is a difference of at least 10 dB in the mechanical impedance between the switched on and switched off conditions.

Figure 2:
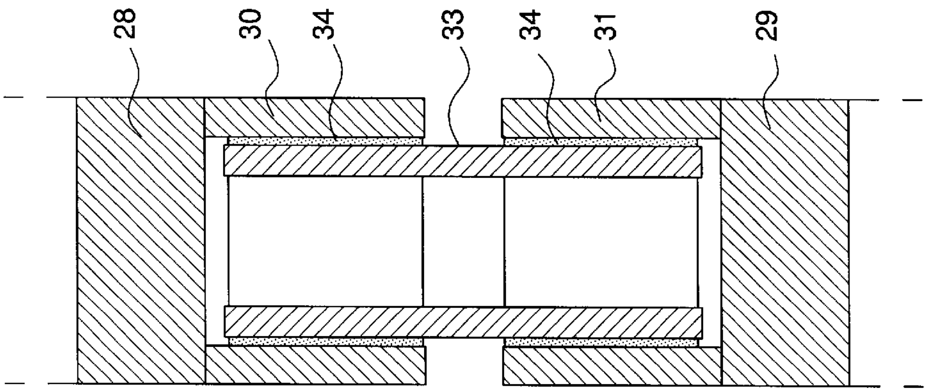
FIG. 2 shows an embodiment of a switchable clutch arrangement using an active piezo element.

FIG. 2 shows an embodiment in which the clutch arrangement 22 is incorporated into the coupling rod 20. The coupling rod 20 comprises a pair of axially aligned, closely axially spaced coupling rod portions 28 and 29. Mutually facing end sections 30 and 31, respectively, of the coupling rod portions 28 and 29 are tube-shaped and have equal inner and outer diameters. The two tube-shaped end sections 30 and 31 receive an active piezoelectric element 33 which, in the present embodiment, has an annular cross-section. The lengths of the end sections 30 and 31 and of the piezoelectric element 33 are dimensioned such that the free ends of the piezoelectric element 33 are axially spaced from the junctions between the end sections 30 and 31 and the respective subsequent solid sections of the coupling rod portions 28 and 29. The outer diameter of the piezoelectric element 33 is only slightly smaller than the inner diameter of the tube-shaped end sections 30 and 31 of the coupling rod 20. The remaining space is filled with a compressible polymer 34 which, in its non-compressed state, is soft and thus has a low mechanical impedance. When the piezoelectric element 33 is electrically activated, i.e. when the clutch arrangement 22 is switched on, the piezoelectric element 33 expands and generates a high radial force acting on the polymer 34, whereby the polymer 34 is heavily compressed. The material of the polymer 34 is selected such that in a compressed state it has a distinctly increased stiffness and thus a higher mechanical impedance when compared with the non-compressed state when the piezoelectric element 33 is not electrically activated, i.e. when the clutch arrangement 22 is switched off.

It is obvious to the one skilled in the art that the design of the switchable clutch arrangement may be modified in numerous ways. Preferably, the clutch arrangement is manufactured using Microsystems engineering techniques.

Figure 3:
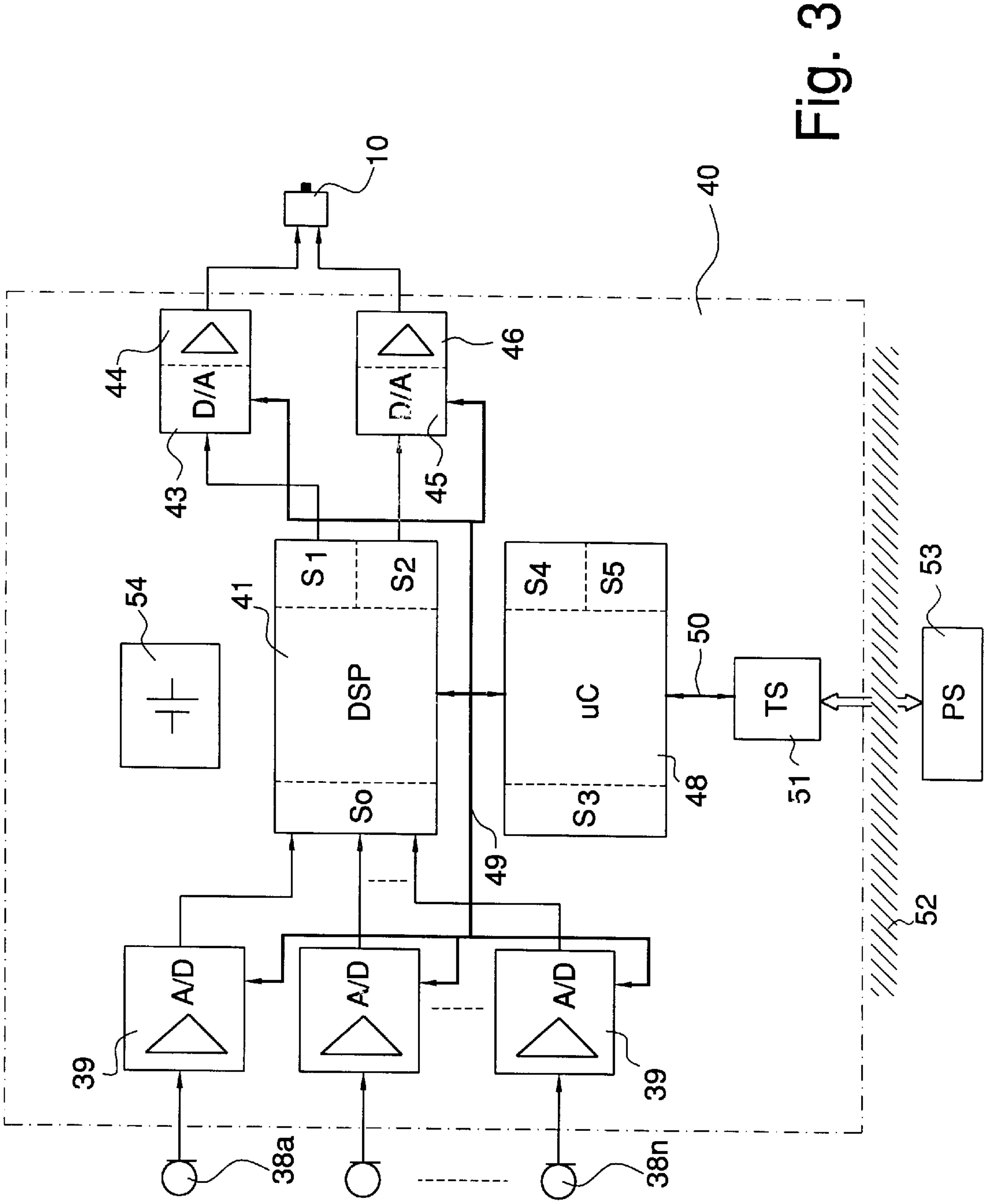
FIG. 3 shows a block diagram of a partially or fully implantable hearing system.

FIG. 3 shows a schematic block diagram of an at least partially implantable hearing system for rehabilitation of a middle and/or inner ear hearing disorder or of a tinnitus, the system being designed for direct mechanical stimulation of a middle ear ossicle and being provided with an arrangement of the type illustrated in FIGS. 1 and 2.

The external acoustic signal is picked up via one or more acoustic sensors (microphones) 38*a* to 38*n* and is converted into electrical analog signals. In an implant exclusively intended for rehabilitation of a tinnitus by masking or noiser functions without an additional hearing aid function, these pick up functions are dispensed with. The electrical sensor signals are routed to units 39 which are part of an implantable electronic module 40 and in which the sensor signal or signals, respectively, is (are) selected, preprocessed, especially pre-amplified, and converted into digital signals (A/D conversion). This preprocessing can comprise, for example, an analog linear or nonlinear pre-amplification and filtering (for example, anti-aliasing filtration). The digitized sensor signals are sent to a digital signal processor 41 (DSP) which provides for the intended functions of the hearing implant, such as e.g. audio signal processing in a system for inner ear hearing impairment and/or signal generation in the case of a tinnitus masker or noiser. The signal processor 41 contains a read-only-memory area $S_0$ which cannot be overwritten, in which the instructions and parameters necessary for "minimum operation" of the system are stored, and a storage area $S_1$ in which the operating software of the intended function or functions of the implant system are stored. Preferably, this storage area is provided twice ($S_1$ and $S_2$). The rewriteable program storages $S_1$ and $S_2$ for storing the operating software can be based on EEPROM or on RAM cells, and in the latter case provisions should be made for this RAM area to always be "buffered" by the power supply system within the implant.

The digital output signals of the signal processor 41 are converted in a digital-to-analog converter (D/A) 43 into analog signals. Dependent on the function of the implant, more than one such digital-analog converter may be provided, or such a digital-analog converter may be completely dispensed with, for example in the case of a hearing system having an electromagnetic output transducer to which a serial, e.g. pulse width modulated, digital output signal of the signal processor 41 is directly routed. The analog output signal of the digital-to-analog converter 43 is then supplied to a driver unit 44 which, dependent on the function of the implant, controls the electromechanical output transducer 10 for stimulating the middle ear or the inner ear. A further output signal of the signal processor 41 controls, via a further digital-to-analog converter 45 and an associated driver unit 46, the switchable clutch arrangement 22 which is disposed within the housing 11 of transducer 10.

In the embodiment illustrated in FIG. 3 the signal processing components 39, 41, and 43 to 46 are controlled, via a bidirectional data bus 49, by a microcontroller ($\mu$C) 48 comprising one or two associated storages $S_4$ and $S_5$, respectively. Especially, the operating software portions of the implant management system, for example, administration, monitoring and telemetry functions, can be stored in the storage areas $S_4$ and $S_5$. Storages $S_1$ and/or $S_2$ can also store patient-specific, for example audiological adaptation parameters which can be altered from the outside. Microcontroller 48 further includes a rewriteable storage $S_3$ in which an operating program for the microcontroller 48 is stored.

The microcontroller 48 communicates via a bidirectional data bus 50 with a telemetry system (TS) 51. This telemetry system 51 in turn wirelessly, bidirectionally communicates through the closed skin indicated at 52, e.g. via an inductive coil coupling not shown, with an external programming system (PS) 53. The programming system 53 advantageously can be a PC-based system with corresponding programming, processing, display and administration software. Via this telemetry interface the operating software of the implant system which is to be changed or completely replaced is transmitted and at first buffered in the storage area $S_4$ and/or $S_5$ of the microcontroller 48. Thus, for example, the storage area $S_5$ may be used for complementary storing of the data transmitted by the external system, and a simple verification of software transmission can be accomplished by a reading process via the telemetry interface to check the coincidence of the contents of the storage areas $S_4$ and $S_5$ before the content of the rewriteable storage $S_3$ is changed or replaced.

In conformity with the presently used nomenclature, the operating software of the at least partially implantable hearing system is intended to include the operating software of the microcontroller 48 (e.g. housekeeping functions such as energy management or telemetry functions) as well as the operating software of the digital signal processor 41. Thus for example a simple verification of software transmission can be accomplished by a reading process via the telemetry interface before the operating software or corresponding signal processing portions of this software are transmitted via data bus 49 into the program storage area $S_1$ of the digital signal processor 41. Furthermore, also the operating program for the microcontroller 48, which for example is stored in the rewriteable storage $S_3$, may be totally or partly changed or replaced with the aid of the external unit 53 via the telemetry interface 51.

All the electronic components of the implant system are supplied with electrical operating energy by a primary or secondary battery 54.

Figure 4:
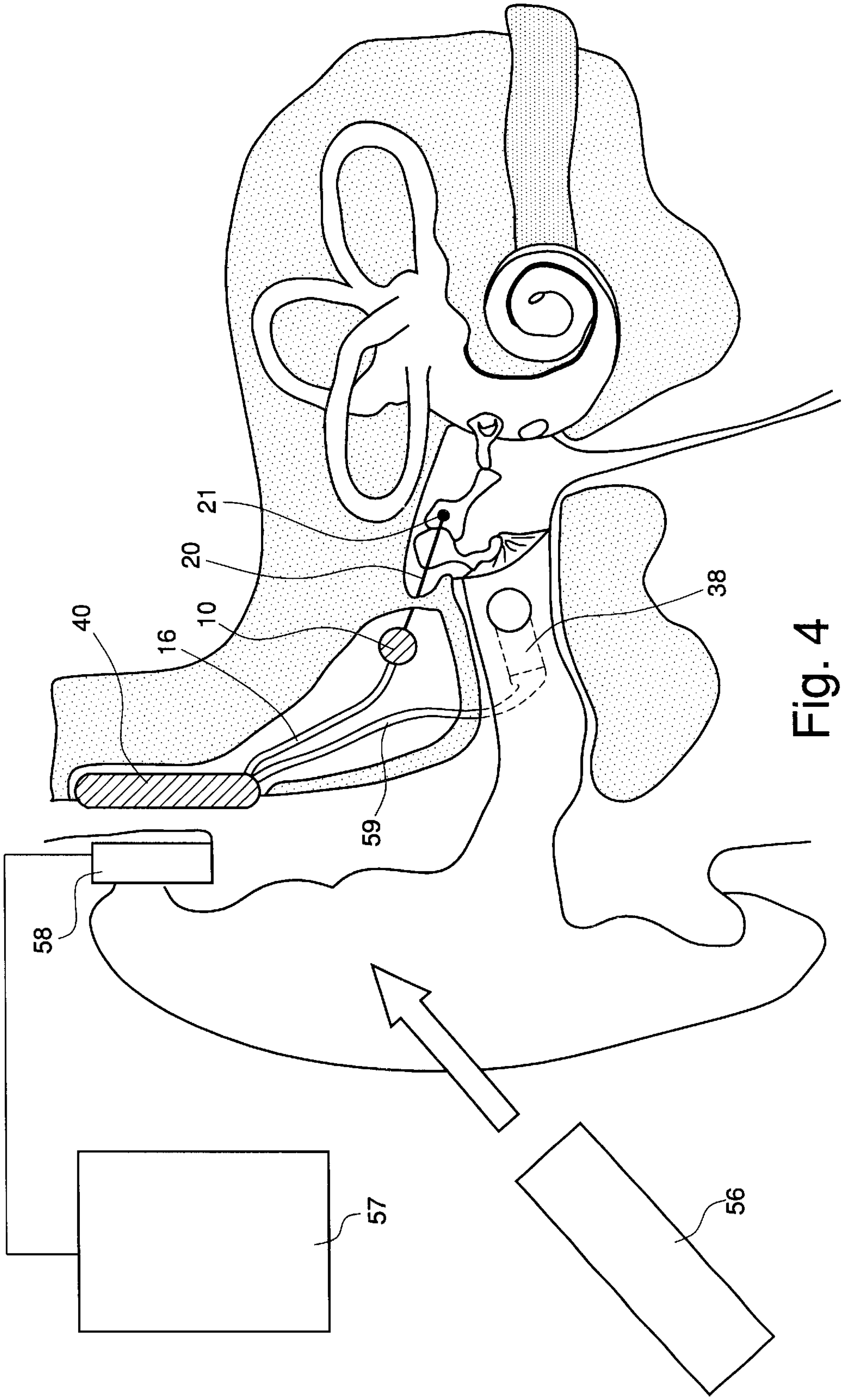
FIG. 4 shows a fully implantable hearing system including an electromechanical transducer for middle ear stimulation as well as a remote control unit and a charging device.

FIG. 4 schematically shows the structure of a completely implantable hearing system comprising as a stimulating actor arrangement an electromechanical output transducer 10, e.g. a transducer in conformity with FIG. 1. Generally, the electromechanical output transducer may be any v, electrodynamic, piezoelectric, magnetostrictive or dielectric (capacitive) transducer. Amongst others, the transducer 10 shown in FIG. 1 may be modified in the manner disclosed in commonly owned U.S. Pat. No. 6,123,660 which is hereby incorporated by reference, so that a permanent magnet is attached to the side of the piezoelectric ceramic disk 13 which in FIG. 1 is the bottom side, with this permanent magnet cooperating with an electromagnetic coil in the manner of an electromagnetic transducer. Such a combined piezoelectric/electromagnetic transducer is of particular advantage with regard to a broad frequency band and to obtaining relatively large oscillation amplitudes at relatively small amounts of supplied energy. The electromechanical output transducer also may be an electromagnetic transducer arrangement as disclosed in commonly owned U.S. Pat. No. 6,162,169 which is hereby incorporated by reference. In each case the presently discussed clutch arrangement 22 additionally is provided for.

To couple the electromechanical transducer 10 to the middle ear or inner ear, especially coupling arrangements as described in commonly owned U.S. Pat. No. 5,941,814 which is hereby incorporated by reference, are suited in which a coupling element, in addition to a coupling part for the pertinent coupling site, has a crimp sleeve which is first slipped loosely onto a rod-shaped part of a coupling rod connected to the transducer in the above described manner. This rod-shaped part of the coupling rod is provided with a rough surface. During implantation, the crimp sleeve can simply be pushed and turned relative to the coupling rod to exactly align the coupling part of the coupling element with the intended coupling site. Then, the crimp sleeve is fixed by being plastically cold-deformed by means of a crimping tool. Alternatively, the coupling element can be fixed with reference to the coupling rod by means of a belt loop which can be tightened.

Other coupling arrangements which can be preferably used here are described, in particular, in commonly owned, co-pending U.S. patent application Ser. Nos. 09/576,009, 09/626,745, 09/613,560, 09/680,489 and 09/680,488, all of which hereby are incorporated by reference. Thus, according to commonly owned, co-pending U.S. patent application Ser. No. 09/576,009, the coupling element can have a contact surface on its coupling end which has a surface shape which is matched or can be matched to the surface shape of the coupling site, and has a surface composition and surface size such that, by placing the coupling end against the coupling site, dynamic tension-compression force coupling of the coupling element and ossicular chain occur due to surface adhesion which is sufficient for secure mutual connection of the coupling element and the ossicular chain.

The coupling element can be provided with an attenuation element which adjoins the coupling site in the implanted state, with entropy-elastic properties in order to achieve the optimum form of vibration of the footplate of the stapes or the membrane which closes the round window or an artificial window in the cochlea, in the vestibulum or in the labyrinth and especially to minimize the risk of damage to the natural structures in the area of the coupling site during and after implantation (see commonly owned, co-pending U.S. patent application Ser. No. 09/626,745).

According to commonly owned co-pending U.S. patent application Ser. No. 09/613,560 the coupling element can be provided with an actuation device for selectively moving the coupling element between an open position, in which the coupling element can engage and disengage the coupling site, and a closed positioning, in which the coupling element in the implanted state is connected by force-fit and/or form-fit to the coupling site.

Furthermore, for mechanically coupling the electromechanical transducer to a pre-selected coupling site on the ossicular chain, a coupling arrangement (see commonly owned, co-pending U.S. patent application Ser. No. 09/680,489) is suitable which has a coupling rod which can be caused to mechanically vibrate by the transducer and a coupling element which can be connected to the pre-selected coupling site. The coupling rod and the coupling element are interconnected by at least one coupling, and at least one section of the coupling element which adjoins the coupling site in the implanted state is designed for low-loss delivery of vibrations to the coupling site, the first half of the coupling having an outside contour with at least roughly the shape of a spherical dome which can be accommodated in the inside contour of a second coupling half that is at least partially complementary to the outside contour. The coupling has the capacity to swivel and/or turn reversibly against the forces of friction, but is essentially rigid for the dynamic forces which occur in the implanted state.

According to a modified embodiment of such a coupling arrangement (see commonly owned, co-pending U.S. patent application Ser. No. 09/680,488) the first half of the coupling has an outside contour with an at least cylindrical, preferably circularly cylindrical, shape which can be accommodated in the inside contour of a second coupling half that is at least partially complementary to the outside contour. A section of the coupling element, which adjoins the coupling site in the implanted state, is designed for low-loss delivery of vibrations to the coupling site in the implanted state, transmission of dynamic forces between the two halves of the coupling taking place essentially in the direction of the lengthwise axis of the first coupling half The coupling can be reversibly coupled and de-coupled, and can be reversibly moved linearly and/or rotationally with reference to the lengthwise axis of the first coupling half, but is rigid for the dynamic forces which occur in the implanted state.

The fully implantable hearing system shown in FIG. 4 further comprises an implantable microphone (sound sensor) 38, a wireless remote control 56 to control the implant functions by the implant wearer, and charging system comprising a charger 57 and a charging coil 58 for wireless transcutaneous recharging of a secondary battery 54 (FIG. 3) located in the implant for power supply of the hearing system.

The microphone 38 can advantageously be built in the manner known from commonly owned U.S. Pat. No. 5,814,095 which hereby is incorporated by reference. Particularly, microphone 38 can be provided with a microphone capsule which is accommodated hermetically sealed on all sides within a housing, and with an electrical feed-through connector for routing at least one electrical connection from within the housing to the outside thereof The housing has at least two legs which are arranged at an angle relative to one another, a first one of the legs containing the microphone capsule and being provided with a sound inlet membrane, and a second one of the legs containing the electrical feed-through connector and being set back relative to the plane of the sound inlet membrane. The geometry of the microphone housing is chosen such that when the microphone is implanted in the mastoid cavity the leg which contains the sound inlet membrane projects from the mastoid into an artificial hole in the posterior bony wall of the auditory canal and the sound inlet membrane touches the skin of the wall of the auditory canal. To fix the implanted microphone 38, there can preferably be a fixation element of the type known from commonly owned U.S. Pat. No. 5,999,632 which hereby is incorporated by reference. This fixation element has a sleeve, a cylindrical housing part of which surrounds the leg which contains the sound inlet membrane, wherein the sleeve is provided with projecting, elastic flange parts which can be placed against the side of the wall of the auditory canal facing the skin of the auditory canal. The fixation element preferably comprises a holding device which, before implantation, maintains the flange parts mentioned above, against the elastic restoration force of the flange parts, in a bent position which allows insertion through the hole of the wall of the auditory canal.

The charging coil 58 connected to the output of the charging device 57 preferably forms part of the transmitting serial resonant circuit in the manner known from commonly owned U.S. Pat. No. 5,279,292 which hereby is incorporated by reference. The transmitting serial resonant circuit can be inductively coupled to a receiving serial resonant circuit which is not shown. The receiving serial resonant circuit can be part of the electronic module 34 in the embodiment as shown in FIG. 2, and according to U.S. Pat. No. 5,279,292, can form a constant current source for the battery 25. The receiving serial resonant circuit is connected in a battery charging circuit which, depending on the respective phase of the charging current flowing in the charging circuit, is closed via one branch or the other of a full wave rectifier bridge.

The electronic module 40 is connected in the arrangement as shown in FIG. 4 via a microphone line 59 to the microphone 38 and via the transducer line 16 to the electromechanical transducer 10 and to the switchable clutch arrangement 22 which preferably likewise is disposed within the transducer housing.

Figure 5:
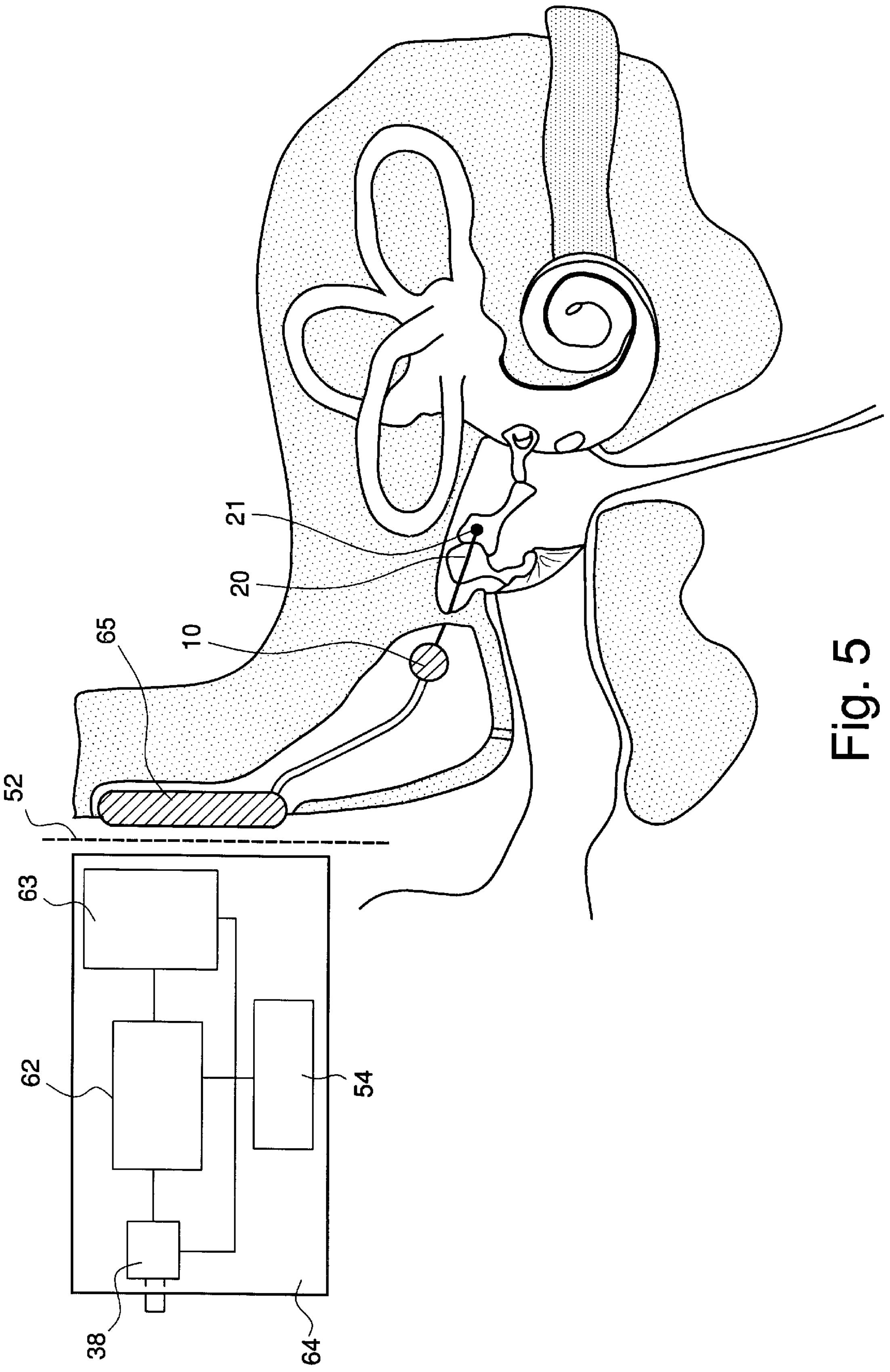
FIG. 5 shows a partially implantable hearing system including an electromechanical transducer for middle ear stimulation.

FIG. 5 schematically shows the structure of a partially implantable hearing system. This partially implantable system includes a microphone 38, an electronic module 62 for electronic signal processing for the most part according to FIG. 3 (but without the telemetry system 51), the power supply (battery) 54 and a modulator/transmitter unit 63 in an external module 64 which is to be worn externally on the body, preferably on the head over the implant. As in the known partial implants, the implant is passive in terms of energy. Its electronic module 65 (without the battery 54) receives its operating energy and control signals for the transducer 10 via the modulator/transmitter unit 63 in the external part 64.

Both the fully implantable hearing system and the partially implantable hearing system may be designed as a monaural system (as illustrated in FIGS. 4 and 5) or as a binaural system. A binaural system for rehabilitation of a hearing disorder of both ears comprises a pair of system units, each of which units is associated to one of the two ears. Both system units may be essentially identical to one another. But the one system unit can also be designed as a master unit and the other system unit as the slave unit which is controlled by the master unit. The signal processing modules of the two system units can communicate with one another in any way, especially via a wired implantable line connection or via a wireless connection, preferably a bidirectional high frequency path, a bodyborne sound-coupled ultrasonic path or a data transmission path which uses the electrical conductivity of the tissue of the implant wearer, such that in both system units optimized binaural signal processing is achieved.

Particularly, the following possibilities of combinations are possible:

Both electronic modules may each contain a digital signal processor according to the aforementioned description, and the operating software of the two processors can be transcutaneously changed, as described. Then the connection of the two modules provides essentially for data exchange for optimized binaural signal processing, for example, of the sensor signals.

Only one module contains the described digital signal processor. The module connection then provides, in addition to transmission of sensor data for binaural sound analysis and balancing, for transfer of the output signal to the contralateral transducer, wherein the latter module can house the electronic transducer driver. In this case, the operating software of the entire binaural system is filed in only one module, and the software also is changed transcutaneously only in this module from the outside via a telemetry unit which is present on only one side. In this case, the power supply of the entire binaural system can be housed in only one electronic module with power being supplied by wire or wirelessly to the contralateral module.

While various embodiments in accordance with the present invention have been shown and described, it is understood that the invention is not limited thereto. These embodiments may be changed, modified and further applied by those skilled in the art. Therefore, this invention is not limited to the details shown and described previously but also includes all such changes and modifications which are encompassed by the appended claims.

We claim:

1. An at least partially implantable hearing system for rehabilitation of a hearing disorder, comprising:

at least one acoustic sensor for picking up an acoustic signal and converting it into an electrical audio sensor signal, an electronic signal processing unit for audio signal processing and amplification, the signal processing unit including an electronic driver arrangement, an electrical power supply unit which supplies individual components of the system with energy, and at least one electromechanical output transducer driven by the electronic driver arrangement and having a mechanical output impedance, said transducer being provided with an active electromechanical element and an output member for stimulating, via a passive coupling element, an ossicle of a middle ear ossicular chain, which chain has a natural capability for vibratory movement, wherein a switchable clutch arrangement is disposed between the active electromechanical element of the transducer and the passive coupling element, and wherein in an inactive condition of the electronic driver arrangement the clutch arrangement disconnects the passive coupling element from the output member of the transducer to such an extent that the mechanical output impedance of the transducer has substantially no influence on the natural capability of the ossicular chain for vibratory movement.

2. The system as claimed in claim 1, wherein the hearing system, upon at least partial implantation thereof, has coupled thereto a biological structure of at least one of a middle ear and an inner ear, said biological structure defining a mechanical load impedance, and wherein the hearing system has a mechanical output impedance which is higher than said mechanical load impedance.

3. The system as claimed in claim 1, wherein the mechanical load impedance acting on the output member of the transducer when the clutch arrangement is activated, is at least 10 dB higher than the mechanical load impedance acting on the output member of the transducer when the clutch arrangement is deactivated.

4. The system as claimed in claim 1, wherein the clutch arrangement comprises an electromechanically active member.

5. The system as claimed in claim 4, wherein the electromechanically active member of the clutch arrangement comprises a piezoelectric element.

6. The system as claimed in claim 1, wherein the active electromechanical element of the transducer and the clutch arrangement are housed in a common casing.

7. The system as claimed in claim 1, wherein the passive coupling element and the active electromechanical element of the transducer are mechanically interconnected via a coupling rod.

8. The system as claimed in claim 7, wherein the clutch arrangement is incorporated into the coupling rod.

9. The system as claimed in claim 7, wherein the clutch arrangement is disposed between the active electromechanical element of the transducer and the end of the coupling rod facing the transducer.

10. The system as claimed in claim 1, wherein the clutch arrangement is controlled by the electronic signal processing unit.

11. The system of claim 1, comprising a telemetry means for transmission of data between an implanted part of the system and an external unit.

12. The system as claimed in claim 1, wherein the electronic signal processing unit comprises a digital signal processor which provides for controlling the clutch arrangement and for at least one function selected from the group consisting of processing electrical audio sensor signals or generation of digital signals for tinnitus masking.

13. The system as claimed in claim 12, wherein a rewritable implantable storage arrangement is assigned to the signal processor for storage and retrieval of an operating program and at least parts of the operating program are adapted to be at least partially replaced by data transmitted from an external unit via a telemetry means.

14. The system of claim 13, further comprising a buffer storage arrangement in which data transmitted from the external unit via the telemetry means are buffered before being relayed to the signal processor.

15. The system of claim 14, further comprising a checking logic for checking data stored in the buffer storage arrangement before said data are relayed to the signal processor.

16. The system of claim 12, comprising a microprocessor module for control of at least one of said digital signal processor and the clutch arrangement, via a data bus.

17. The system of claim 15, comprising a microprocessor module for control of at least one of said digital signal processor and the clutch arrangement, via a data bus; wherein the checking logic and the buffer storage arrangement are implemented in the microprocessor module.

18. The system of claim 12, comprising a microprocessor module for control of at least one of said digital signal processor and the clutch arrangement, via a data bus; wherein at least one of a plurality of program parts are adapted to be transferred between an external source, the microprocessor module and the signal processor via the data bus and a telemetry means.

19. The system of claim 16, wherein an implantable storage arrangement for storage of an operating program for the microprocessor module is assigned to the microprocessor module, and at least one of a plurality of parts of the operating program for the microprocessor module are adapted to be replaced by data transferred from an external unit via a telemetry means.

20. The system of claim 13, comprising at least two storage areas for storage and retrieval of at least said operating program of the signal processor.

21. The system of claim 14, wherein the buffer storage arrangement comprises at least two storage areas for storage and retrieval of data transferred from the external unit via the telemetry means.

22. The system of claim 12, wherein a preprogrammed read-only memory area is assigned to the signal processor.

23. The system of claim 11, wherein the telemetry means is adapted for transmission of operating parameters between the implantable part of the system and the external unit.

24. The system of claim 1, wherein the electrical power supply unit comprises an implantable rechargeable energy storage element, and wherein the system is totally implantable except for a wireless, transcutaneous charging device which is provided for charging of the storage element.

25. The system of claim 24, comprising a wireless remote control for control of implant functions by the implant wearer.

26. The system of claim 1, wherein the system is partially implantable, wherein said at least one acoustic sensor, said electronic signal processing unit, said power supply unit and a modulator/transmitter unit are contained in an external module to be worn externally on the body of a user, and wherein the at least one electromechanical output transducer is an implantable passive unit which receives operating energy and control data for the transducer and the clutch via the modulator/transmitter unit in the external module.

* * * * *